United States Patent [19]

Kusano et al.

[11] Patent Number: 4,851,382

[45] Date of Patent: Jul. 25, 1989

[54] SEPARATION MEDIUM

[75] Inventors: Hiroshi Kusano; Hideaki Kiniwa, both of Yokohama; Akihiro Shimura, Machida; Masahiko Annaka, Mitaka, all of Japan

[73] Assignee: Mitsubishi Kasei Corporation, Japan

[21] Appl. No.: 221,300

[22] Filed: Jul. 19, 1988

[30] Foreign Application Priority Data

Jul. 21, 1987 [JP] Japan ................................ 62-181318

[51] Int. Cl.$^4$ ............................................. B01J 20/22
[52] U.S. Cl. .................................. 502/401; 502/402; 502/403
[58] Field of Search ..................... 501/401, 402, 403

[56] References Cited

U.S. PATENT DOCUMENTS

| | | | |
|---|---|---|---|
| 4,324,681 | 4/1982 | House | 502/401 X |
| 4,525,465 | 6/1985 | Someno et al. | 502/403 X |
| 4,654,322 | 3/1987 | Holbein et al. | 502/401 X |
| 4,767,670 | 8/1988 | Cox et al. | 502/401 X |
| 4,793,921 | 12/1988 | Hauck et al. | 502/401 X |

Primary Examiner—Patrick P. Garvin
Attorney, Agent, or Firm—Jordan B. Bierman

[57] ABSTRACT

A separation medium useful as an adsorbent of liquid chromatography for optical resolution of racemic mixtures is disclosed, which comprises a reversed phase support coated with an optically active amino acid derivative represented by formula (I):

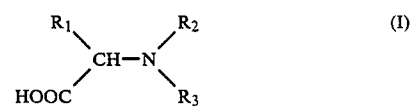

wherein $R_1$ represents a straight or branched alkyl group having from 1 to 3 carbon atoms; and $R_2$ and $R_3$ each represents a straight or branched alkyl group having from 4 to 12 carbon atoms which may contain an aromatic group or an unsaturated alkyl group.

The separation medium is applicable to optical resolution of a wide range of DL-amino acids and exhibits excellent durability.

7 Claims, 2 Drawing Sheets

RETENTION TIME (MINUTES)

1

SEPARATION MEDIUM

FIELD OF THE INVENTION

This invention relates to a separation medium to be used as an absorbent of liquid chromatography for racemic resolution and, more particularly to a separation medium useful for separation analysis of DL-amino acids.

BACKGROUND OF THE INVENTION

It is known to use a silica gel support for reversed phase chromatography (hereafter referred to as reversed phase support) coated with an amino acid derivative as a medium for optical resolution, as described, e.g., in V. A. Davankov, *Chromatographia*, Vol. 13, 667 (1980) or JP-A-58-96062 (The term "JP-A" as used herein means an "unexamined published Japanese patent application"). The references teach use of an N-alkyl derivative of proline or hydroxproline for coating the support.

However, difficulty arises in coating these amino acid derivatives on the reversed phase support because they have high crystallinity and, therefore, low solubility in an aqueous alcohol solution chiefly employed for the coating. Besides, the coated packing material exhibits so poor stability that the amino acid derivative carried on the support falls off during long-term use, resulting reduction of optical resolution ability. Further, this packing, although excellent in resolution of specific amino acids, scarecely manifests the resolving ability to hydrophilic amino acids, such as serine, histidine, lysine, glutamic acid, etc.

SUMMARY OF THE INVENTION

One of the objectives of this invention is to provide a separation medium which is excellent in durability and applicable to optical resolution of a broader scope of amino acids.

Another objective of this invention is to provide a separation medium which can be prepared easily.

This invention provides a separation medium comprising a reversed phase support coated with an optically active amino acid derivative represented by formula (I):

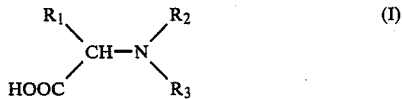

wherein $R_1$ represents a straight or branched alkyl group having from 1 to 3 carbon atoms; and $R_2$ and $R_3$, which may be the same or different, each represents a straight or branched alkyl group having from 4 to 12 carbon atoms which may contain an aromatic group or an unsaturated alkyl group.

DETAILED DESCRIPTION OF THE INVENTION

Figure 1:
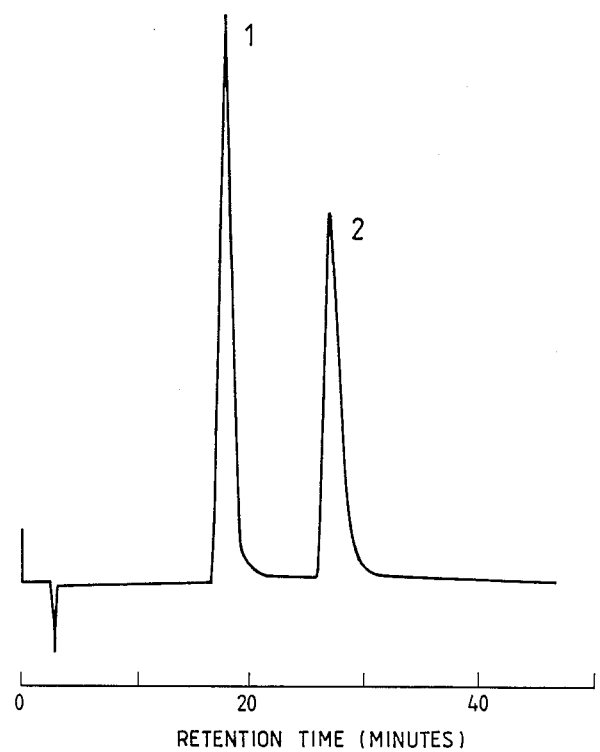
FIGS. 1 and 2 each shows a chromatogram obtained in Example 2. In the Figs., the ordinate indicates an absorbance at 254 nm, and the abscissa a retention time.

The optically active amino acid derivative represented by formula (I) can be prepared by converting a primary amino group of an optically active amino acid to a tertiary amino group by substituting the two hydrogen atoms thereof with an alkyl group. The starting amino acids include D- or L-forms of alanine ($R_1=CH_3$), α-aminobutyric acid ($R_1=CH_2CH_3$), valine ($R_1=CH(CH_3)_2$), norvaline ($R_1=(CH_2)_2CH_3$), serine ($R_1=CH_2OH$), threonine ($R_1=CH(OH)CH_3$), etc.

The alkyl groups ($R_2$ and $R_3$) for substituting the two hydrogen atoms of the primary amino group of these optically active amino acids are selected from those having from 4 to 12 carbon atoms. In general, as the chain length of the alkyl group becomes longer to have higher hydrophobic properties, the bonding force to the reversed phase support is strengthened to suppress release of the amino acid derivative and to enhance durability of the separation medium but, in turn, solubility in solvents (e.g., an aqueous alcoholic solution) becomes lower to make the coating difficult. Further, the coverage expressed in terms of mole number relatively decreases, resulting in reduced resolving ability. Therefore, it is preferable to make the chain length of the above-described alkyl group longer in the case of starting with amino acids having low hydrophobic properties or shorter in the case of starting with those having high hydrophobic properties.

More specifically, when the amino acid has low hydrophobic properties, namely has one carbon atom in its alkyl group represented by $R_1$, the alkyl groups to be introduced, $R_2$ and $R_3$, are preferably selected so that they contain from 10 to 20 carbon atoms in total. On the other hand, when the amino acid has high hydrophobic properties, namely has 2 or 3 carbon atoms in $R_1$, the alkyl groups to be introduced, $R_2$ and $R_3$ are preferably selected so that they contain from 8 to 14 carbon atoms in total. The alkyl groups $R_2$ and $R_3$ may not always be the same.

These alkyl groups are not restricted in structure and may be either straight or branched chain and may contain an aromatic group or an unsaturated alkyl group in so far as they have adequate hydrophobic properties.

Introduction of the alkyl groups to the primary amino group of the optically active amino acid can be carried out by a process comprising reacting the optically active amino acid with a halide of an alkyl group, i.e., an alkyl halide, in the presence of an alkali metal salt as disclosed in Soviet Union Pat. No. 3,356,004; a process comprising reacting the optically active amino acid with an aldehyde precursor of an alkyl group under a reductive condition as disclosed in *Analytical Biochemistry*, Vol. 121, 370 (1982); and the like.

The alkyl halide to be used as an alkylating agent in the former process is not limited as long as the alkyl moiety contains from 4 to 12 carbon atoms. Specific examples of usable alkyl halides include a chloride, a bromide or an iodide of a straight chain alkyl group (e.g., butyl, hexyl, octyl, and dodecyl), a branched chain alkyl group (e.g., isobutyl and 2-ethylhexyl), an alkyl group containing an aromatic group or an unsaturated group (e.g., benzyl and pentenyl), etc. The alkali metal salt to be used as a dehalogenating agent preferably includes sodium hydroxide and potassium hydroxide. The alkali metal salt is preferably used in the form of a concentrated aqueous solution.

The aldehyde precursor to be reacted under a reductive condition according to the latter process is not limited as long as the alkyl moiety thereof contains from 4 to 12 carbon atoms. Specific examples of such an aldehyde precursor are heptyl aldehyde, octyl aldehyde, nonyl aldehyde, etc. The reductive condition can be created by introduction of hydrogen in the presence of catalyst such as palladium immobilized activated carbon, or the use of a reductive condensating agent, e.g., sodium cyanoborohydride ($NaBH_3CN$), or the like technique. In carrying out the reaction, the starting amino acid is suspended in a medium (e.g., alcohols), the alkyl aldehyde and a palladium-on-carbon are added to the suspension, and the mixture is stirred at about room temperature for 10 to 100 hours while blowing hydrogen thereinto.

In any process, it is preferable to use the above-described alkylating agent in an amount at least twice the molar amount of the amino acid in order to reduce by-production of a monoalkylated product.

The reaction product is desirably purified by column chromatography, for example, on silica gel, or solvent extraction, or distillation or the like technique to thereby remove the by-produced monoalkylated compound, unreacted starting material and the reaction reagent. However, the monoalkylated compound, if produced in a small quantity, should not always be removed, and the reaction product containing the monoalkyled compound may be used as such for the subsequent coating on a support. It should be noted, however, that the dialkylated compound should dominate at least 60% by weight of the resulting amino acid derivative.

The unreacted raw material, etc. may also be removed by washing with a solvent, e.g., an aqueous alcohol solution, after the amino acid derivative is coated on a support.

The reversed phase support on which the dialkylated amino acid is coated may be any of organic or inorganic materials having a hydrophobic surface. Examples of such materials include silica gel having been subjected to surface treatment with an alkylsilane having from 6 to 32 carbon atoms in the alkyl moiety thereof, silica gel carrying a silicone having 6 to 32 carbon atoms in its alkyl moiety, styrene-based or acrylic hydrophobic polymer gel, and hydrophilic acrylic or vinyl alcohol polymer gel having introduced on the surface thereof an alkyl group containing from 6 to 18 carbon atoms.

The shape of the support may be any of a crushed particulate or a bead and may be either porous or nonporous. Preferred is a porous bead having a particle size of from 0.5 to 500 μm, particularly from 1 to 50 μm. By using a porous support with a large surface area, the coverage of the amino acid derivative can be increased and, therefore, a desired coverage can be obtained by controlling the surface area of the support. The porous support preferably has a pore diameter in the range of from 10 to 1,000 Å and a surface area in the range of from 1 to 1,000 $m^2$.

Methods for coating the support with the amino acid derivative include a method comprising introducing an aqueous alcohol solution having dissolved therein the amino acid derivative directly into a column for liquid chromatography packed with the reversed phase support as taught in *Chromatographia*, Vol. 13, 667 (1981); a method comprising mixing the reversed phase support with an alcoholic solution of the amino acid derivative and adding water dropwise to the mixture to thereby precipitate the amino acid derivative on the surface of the support; a method comprising mixing the reversed phase support and a solution of the amino acid derivative and removing the solvent by evaporation under reduced pressure; and the like.

The amino acid derivative is thus coated on the support to a coverage of from 1 to 50% by weight, preferably from 5 to 30% by weight, to the support. Two or more kinds of amino acid derivatives can also be coated on the support.

After the support, coated with the amino acid derivative is converted to a complex salt with an appropriate metallic ion, e.g., $Cu^{2+}$, $Ni^{2+}$, $Zn^{2+}$, $Cd^{2+}$, $Hg^{2+}$ or $Co^{3+}$, it can be used for optical resolution according to a liquid chromatographic technique as stated below.

The coated support, i.e., separation medium, is tightly packed in a 0.5 to 100 cm long column composed of glass, stainless steel, titanium, etc. A feed pump and a sample loader are connected to the inlet of the column, and a detector such as an ultraviolet detector and a polarimeter, and, if desired, a fraction collector are connected to the outlet of the column. A sample solution is loaded into the column, and an eluent is then passed through the column by means of the feed pump to develop and separate a racemic mixture in the column. A suitable eluent includes an aqueous solution of a metal salt, such as a 0.05 to 2 mM aqueous solution of copper sulfate or copper acetate. It is preferable to add a water-miscible organic solvent, e.g., methanol, acetonitrile, etc., to the eluent in an amount up to 30% by volume. According as the amount of the organic solvent added increases, the retention time of the stereoisomers generally tends to decrease. In order to obtain a chromatogram with satisfactory reproducibility, it is very favorable to maintain the pH of the eluent constant. The flow rate of the eluent is usually held at a linear velocity of from 1 to 20 cm/min.

The eluate collected from the column is then forwarded to the detector, such as an ultraviolet detector, where each of the separated enantiomers is detected through its absorbance at, for example, 254 nm, and the chromatogram is recorded by means of a recording equipment.

The substances which can be optically resolved by using the separation medium according to the present invention include not only various amino acids and derivatives thereof but also racemic mixtures capable of coordinating to the above-recited metallic ions, such as α-aminocarboxylic acids, 2-aminoalcohols, β-aminocarboxylic acids, 1,2-diamines, and so on.

The present invention is now illustrated in greater detail with reference to the following Examples and Comparative Examples, but it should be understood that the present invention is not deemed to be limited thereto. In these examples, all the percents are by weight unless otherwise indicated.

EXAMPLE 1

Preparation of Amino Acid Derivative

In 20 ml of ethanol was suspended 2.10 g (20 mmol) of D-serine, and 0.3 g of 10% palladium-on-activated carbon and 5.64 g (44 mmol) of n-octyl aldehyde were added to the suspension. The mixture was allowed to react at 50° C. for 48 hours under stirring while introducing hydrogen gas thereinto. After the reaction, the catalyst was separated by filtration, and the filtrate was concentrated under reduced pressure to obtain 7.41 g of crude N,N-di-n-octyl-D-serine as a fatty and oily product.

Elemental Analysis for $C_{19}H_{39}NO_3$: Found (%): C 67.19; H 11.76; N 4.44; Calcd. (%): C 69.30; H 11.85; N 4.26.

The infrared absorption spectrum of the product showed a strong absorption assigned to C—H stretching vibration at 2850 to 2925 cm$^{-1}$ and an absorption assigned to COOH at 1710 cm$^{-1}$. From these results combined with the elemental analysis, the product was identified to be N,N-di-n-octyl-D-serine.

Preparation of Separation medium

A mixture of methanol and water (15:85 by volume) was passed through a stainless steel column (inner diameter: 4.6 mm; height: 50 mm) packed with 0.45 g of porous silica gel having an average particle size of 5 μm and having been subjected to surface treatment with octadecylsilane. Then, 2.5 ml of a 5% methanolic solution containing the above-prepared N,N-di-n-octyl-D-serine was passed through the column. The column was washed with the same methanol-water mixture as used above to thereby obtain a column packed with a separation medium containing 20% of N,N-di-n-octyl-D-serine on its surface. The column was treated with 1.8 ml of a saturated solution of copper acetate in the same methanol-water mixture as used above and washed thoroughly with a 0.1 mmol/1 aqueous solution of copper sulfate.

Racemic Resolution

To the thus obtained column packed with a separation medium was applied 20 μl of a 0.5 mmol/1 aqueous solution of each of racemic mixtures of amino acids shown in Table 1 below, and a 0.1 mmol/1 aqueous solution of copper sulfate was fed to the column as an eluent at a flow rate of 1.0 ml/min at 30° C. to develop the racemic mixtures. The eluate was detected by means of an ultraviolet detector at a wavelength of 254 nm. The results of racemic resolution are shown in Table 1.

In Table 1, the terminology "retention time" means a time from the introduction of the racemic mixture through elution of each enantiomer, that is, a retention time of each enantiomer in the column. The terminology "separation factor α" is a measure of resolving ability of the separation medium and can be expressed by the following equation:

$$\alpha = \frac{T_2 - T_0}{T_2 - T_0}$$

wherein $T_1$ is a retention time of an enantiomer, which is more weakly adsorbed; $T_2$ is a retention time of an enantiomer which is more strongly adsorbed; and $T_0$ is a retention time corresponding to a dead volume of the column.

When α=1, the separation medium has no resolving ability at all. The greater the α value than 1, the higher the resolving ability.

TABLE 1

| DL-Amino Acid | Retention Time (min) | | Separation Factor α* |
|---|---|---|---|
| | L-Amino Acid | D-Amino Acid | |
| Histidine | 20.96 | 23.27 | 1.12 |
| Serine | 18.16 | 24.52 | 1.39 |
| Alanine | 23.66 | 29.10 | 1.25 |
| Aspartic acid | 38.59 | 41.86 | 1.09 |
| Ornithine | 9.30 | 11.74 | 1.32 |
| Arginine | 17.20 | 23.94 | 1.43 |
| Citrulline | 34.96 | 56.31 | 1.64 |

TABLE 1-continued

| DL-Amino Acid | Retention Time (min) | | Separation Factor α* |
|---|---|---|---|
| | L-Amino Acid | D-Amino Acid | |
| Glutamic acid** | 41.67 | 67.20 | 1.64 |

Note:
*$T_0$ = 1.66 min
**A 0.5 mmol/1 copper sulfate aqueous solution was used as an eluent.

EXAMPLE 2

Preparation of Amino Acid Derivative

A mixed suspension consisting of 7.10 g (80 mmol) of L-alanine, 6.9 g (110 mmol) of NaBH$_3$CN, 19.4 g (170 mmol) of n-heptyl aldehyde, and 200 ml of methanol was stirred at room temperature for 50 hours. After the reaction, the reaction solution was purified by column chromatography on silica gel to obtain 21.7 g of N,N-di-n-heptyl-L-alanine as a fatty and oily product.

In the infrared absorption spectrum of the product, an absorption at 3200 to 3600 cm$^{-1}$ based on N—H stretching vibration substantially disappeared, and a strong absorption assigned to C—H stretching vibration of a straight chain alkyl group at 2850 to 2925 cm$^{-1}$ and an absorption assigned to -COO— at 1580 cm$^{-1}$ and 1630 cm$^{-1}$ were observed. The product was thus identified to be a sodium salt of N,N-di-n-heptyl-L-alanine.

Elemental Analysis for C$_{17}$H$_{34}$Na: Found (%): C 64.45; H 11.05; N 4.33; Calcd. (%): C 66.45; H 11.07; N 4.56.

Preparation of Separation Medium

In the same manner as in Example 1, the above obtained N,N-di-n-heptyl-L-alanine was passed through a column (inner diameter: 4.6 mm; height: 50 mm) packed with porous silica gel having an average particle size of 3 μm and having been subjected to surface treatment with octadecylsilane to coat the particles. The separation medium in the column weighed 0.57 g, and the coverage of N,N-di-n-heptyl-L-alanine was found to be 20%.

Racemic Resolution

Each of racemic mixtures shown in Table 2 was resolved by using the above obtained column under the same conditions of Example 1. The results obtained are shown in Table 2.

TABLE 2

| DL-Amino Acid | Separation Factor α | DL-Amino Acid | Separation Factor α |
|---|---|---|---|
| Histidine | 1.59 | Norvaline | 2.20 |
| Serine | 1.25 | α-Aminobutyric acid | 2.07 |
| Alanine | 1.42 | Glutamic acid | 1.47 |
| Threonine | 1.29 | Tyrosine | 1.96 |
| Lysine | 1.37 | Leucine | 2.06 |
| Arginine | 1.63 | Isoleucine | 2.30 |
| Citrulline | 1.85 | Norleucine | 2.26 |
| Proline | 2.16 | Phenylalanine | 1.89 |
| Valine | 2.17 | Tryptophan | 1.90 |

FIG. 1 is a chromatogram showing racemic resolution of DL-glutamic acid. In the Fig., peak Nos. 1 and 2 indicate D-glutamic acid and L-glutamic acid, respectively. While optical resolution of DL-glutamic acid has been difficult to carry out with commercially available columns for amino acid resolution, the chromatogram of FIG. 1 proves that the column packed with the separation medium according to the present invention enables us to completely resolve DL-glutamic acid at high efficiency.

Figure 2:
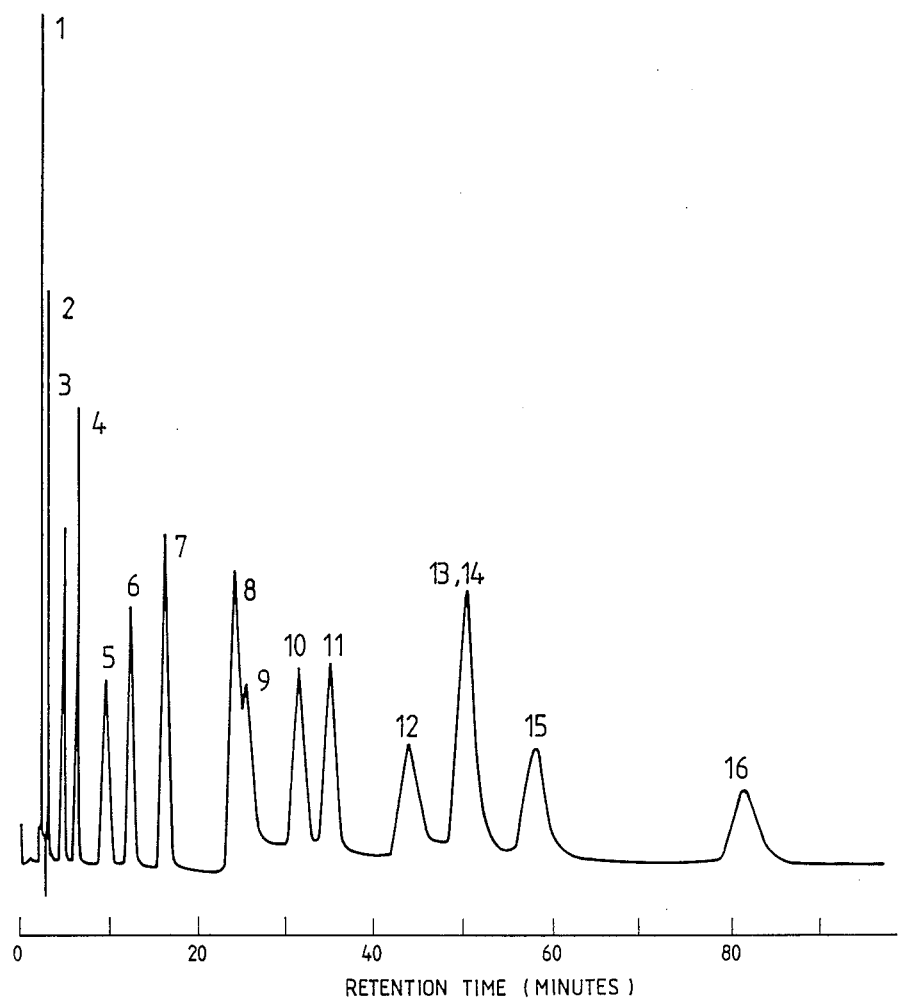

FIG. 2 shows a chromatogram obtained when 8 kinds of amino acids (DL-alanine, DL-proline, DL-valine, DL-leucine, DL-norleucine, DL-tyrosine, DL-ethionine, and DL-phenylalanine) were subjected to racemic resolution all at once using the same column as prepared above. The peak numbers 1 to 16 of the chromatogram correspond to enantiomers as follows.

| | |
|---|---|
| 1 ... D-Alanine | 9 ... D-Tyrosine |
| 2 ... L-Alanine | 10 ... L-Leucine |
| 3 ... D-Proline | 11 ... D-Ethionine |
| 4 ... D-Valine | 12 ... L-Tyrosine |
| 5 ... L-Proline | 13 ... L-Norleucine |
| 6 ... L-Valine | 14 ... D-Phenylalanine |
| 7 ... D-Leucine | 15 ... L-Ethionine |
| 8 ... D-Norleucine | 16 ... L-Phenylalanine |

While it has been extremely difficult to carry out simultaneous optical resolution of plural DL-amino acids with the conventional separation media, it can be seen that the column packed with the separation medium according to the present invention makes it possible to easily perform such simultaneous resolution.

Further, in order to evaluate durability of the separation medium of the present invention, optical resolution of DL-valine was repeatedly run 1000 times using the above prepared column. As an eluent, a 0.5 mmol/l copper sulfate aqueous solution was passed at a flow rate of 1.0 ml/min. The results obtained are shown in Table 3 below.

TABLE 3

| Running Time | Retention Time (min) | | Separation Factor α |
|---|---|---|---|
| | L-Valine | D-Valine | |
| 1 | 14.25 | 7.45 | 1.98 |
| 1000 | 13.98 | 7.36 | 1.97 |

As is shown in Table 3, there is virtually no change in retention time or separation factor between the first running and the 1000th running, proving the separation medium of the present invention extremely excellent in durability.

EXAMPLE 3

Preparation of Amino Acid Derivative

In a mixture of 100 ml of ethanol and 40 ml of water were dissolved 8.0 g (200 mmol) of sodium hydroxide and 11.72 g (100 mmol) of L-norvaline. To the solution was added 27.41 g of 1-bromoethane, and the mixture was heated up to 70° C., followed by vigorously stirring for 5 hours. Thereafter, 4.0 g of sodium hydroxide was added thereto, and the stirring was continued for an additional time of 5 hours under the same condition. After the reaction, the reaction mixture was cooled, adjusted to a pH of 7 with sulfuric acid, and diluted with 1.5 liter of water to obtain N,N-di-n-butyl-L-norvaline as a fatty and oily product.

Elemental Analysis for $C_{13}H_{27}NO_2$: Found (%): C 65.54; H 11.74; N 5.88; Calcd. (%): C 68.12; H 11.79; N 6.11.

Preparation of Separation Medium

In 50 ml of ethanol was dissolved 0.4 g of the above obtained N,N-di-n-butyl-L-norvaline. To the solution was added 1.6 g of porous silica gel having an average particle size of 5 μm and having been subjected to surface treatment with octylsilane. Then, 50 ml of water was added thereto dropwise over a period of about 5 hours to thereby obtain 1.98 g of a separation medium having an amino acid derivative coverage of 19.2%.

Racemic Resolution

The resulting separation medium was packed in a column having an inner diameter of 4.6 mm and a height of 150 mm. Each of racemic mixtures shown in Table 4 below was subjected to resolution using the resulting column under the same conditions of Example 1. The results obtained are shown in Table 4.

TABLE 4

| DL-Amino Acid | Separation Factor α |
|---|---|
| Serine | 1.32 |
| Alanine | 1.29 |

COMPARATIVE EXAMPLE 1

The procedure of Example 1 was repeated, except that N,N-dipropyl-L-alanine synthesized in the same manner as in Example 1 was used as an amino acid derivative for coating the octadecylated silica gel. According as the eluent passed through the column, the N,N-dipropyl-L-alanine was released from the support, ultimately resulting in the failure to effect resolution of the amino acid racemic mixture when 10 liters of the eluent had passed.

COMPARATIVE EXAMPLE 2

In the same manner as in Example 3, N-dodecyl-L-alanine was synthesized and a packed column was prepared. Each of DL-amino acids shown in Table 5 below was subjected to optical resolution using the resulting column under the same conditions of Example 2. The results obtained are shown in Table 5.

TABLE 5

| DL-Amino Acid | Separation Factor α |
|---|---|
| Alanine | 1.05 |
| Glutamic acid | 1.10 |

As is apparent from Table 5 in view of the results of Example 2, the separation factors attained in this example are lower, revealing that a monoalkylated amino acid is inferior to the corresponding dialkylated compound in resolving ability.

COMPARATIVE EXAMPLE 3

In the same manner as in Example 3, N,N-di-n-tetradecyl-L-alanine was synthesized and a packed column was prepared. When each of DL-serine and DL-alanine was subjected to optical resolution using the resulting column under the same conditions of Example 2, the DL-amino acid could not be substantially retained in the column, failing to be resolved.

As stated above, the separation medium of the present invention can be suitably applied to optical resolution of various amino acids by liquid chromatography. The present invention makes it possible to optically resolve a wide range of amino acids including alanine, serine, histidine, glutamic acid, etc. which have been difficult to be resolved by conventional techniques. In addition, the separation medium of the invention is excellent in durability and straightforwardness with which it can be prepared.

While the invention has been described in detail and with reference to specific embodiments thereof, it will be apparent to one skilled in the art that various changes and modifications can be made therein without departing from the spirit and scope thereof.

What is claimed is:

1. A separation medium comprising a reversed phase support coated with an optically active amino acid derivative represented by formula (I):

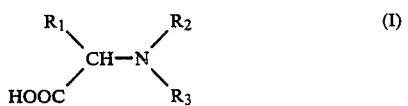

wherein $R_1$ represents a straight or branched alkyl group having from 1 to 3 carbon atoms; and $R_2$ and $R_3$, which may be the same or different, each represents a straight or branched alkyl group having from 4 to 12 carbon atoms which may contain an aromatic group or an unsaturated alkyl group.

2. A separation medium as claimed in claim 1, wherein the total number of carbon atoms contained in $R_2$ and $R_3$ is from 10 to 20 when $R_1$ contains one carbon atom.

3. A separation medium as claimed in claim 1, wherein the total number of carbon atoms contained in $R_2$ and $R_3$ is from 8 to 14 when $R_1$ contains 2 to 3 carbon atoms.

4. A separation medium as claimed in claim 1, wherein said support is a porous support having a particle size of from 1 to 50 μm.

5. A separation medium as claimed in claim 4, wherein said porous support has a pore diameter of from 10 to 1000 Å and a surface area of from 1 to 1000 m².

6. A separation medium as claimed in claim 1, wherein said separation medium has an amino acid derivative coverage of from 1 to 50% by weight to the support.

7. A separation medium as claimed in claim 1, wherein said separation medium has an amino acid derivative coverage of from 5 to 30% by weight to the support.

* * * * *

UNITED STATES PATENT AND TRADEMARK OFFICE
CERTIFICATE OF CORRECTION

PATENT NO. : 4,851,382

DATED : July 25, 1989

INVENTOR(S) : KUSANO, et al

It is certified that error appears in the above-identified patent and that said Letters Patent is hereby corrected as shown below:

Column 1, line 16, change "667" to --677--.

Signed and Sealed this

Fifth Day of June, 1990

Attest:

HARRY F. MANBECK, JR.

Attesting Officer

Commissioner of Patents and Trademarks